United States Patent [19]

Kummer

[11] 4,017,550
[45] Apr. 12, 1977

[54] MANUFACTURE OF 1,4-BUTANEDIOL

[75] Inventor: Rudolf Kummer, Frankenthal, Germany

[73] Assignee: BASF Aktiengesellschaft, Ludwigshafen (Rhine), Germany

[22] Filed: Dec. 30, 1974

[21] Appl. No.: 537,118

[30] Foreign Application Priority Data

Jan. 14, 1974 Germany .......................... 2401553

[52] U.S. Cl. .................. 260/635 E; 260/340.7; 260/346.1 R
[51] Int. Cl.$^2$ .................. C07C 29/00; C07C 29/16
[58] Field of Search ................................ 260/635 E

[56] References Cited

UNITED STATES PATENTS

| | | | |
|---|---|---|---|
| 2,888,492 | 5/1959 | Fischer et al. | 260/635 E |
| 3,239,566 | 3/1966 | Slaugh et al. | 260/635 A |
| 3,448,157 | 6/1969 | Slaugh et al. | 260/635 A |
| 3,773,842 | 11/1973 | Schirmann et al. | 260/635 E |
| 3,929,915 | 12/1975 | Cumbo et al. | 260/635 E |

OTHER PUBLICATIONS

J.F.W. McOmie, Advances in Organic Chem., Interscience Publishers, vol. 3, pp. 264–265, (1963).

*Primary Examiner*—Joseph E. Evans
*Attorney, Agent, or Firm*—Johnston, Keil Thompson & Shurtleff

[57] ABSTRACT

The manufacture of 1,4-butanediol by hydroformylation of cyclic acetals of acrolein in the presence of phosphine-modified cobalt carbonyl complexes or rhodium carbonyl complexes and hydrogenation of the 3-formylpropionaldehyde-acetals which are the principal products first formed.

18 Claims, No Drawings

MANUFACTURE OF 1,4-BUTANEDIOL

This application discloses and claims subject matter described in German Patent Application P 24 01 553.0, filed Jan. 14, 1974, which is incorporated herein by reference.

The present invention relates to a new process for the manufacture of 1,4-butanediol.

In an industrially practised process, 1,4-butanediol is manufactured by reaction of acetylene with formaldehyde in the presence of copper acetylide, to form butynediol which is then hydrogenated to 1,4-butanediol. Since acetylene is becoming increasingly expensive as a starting material for industrial processes, it is desirable to be able to manufacture 1,4-butanediol from less expensive petrochemical feedstocks. Attempts have already been made (c.f. German Published Application 2,217,452), to manufacture 1,4-butanediol by reacting butadiene with acetic acid and molecular oxygen, or gases containing molecular oxygen, in the presence of noble metal catalysts, to form 1,4-butenediol diacetate which is then hydrogenated and saponified. Whilst this process has the advantage of using inexpensive feedstocks, it has hitherto not proved successful in industry.

It is an object of the present invention to provide an advantageous method of obtaining 1,4-butanediol, which is an important material for numerous organic syntheses.

We have found an advantageous method of obtaining 1,4-butanediol, wherein cyclic acetals of acrolein are reacted with carbon monoxide and hydrogen in the presence of cobalt carbonyl complexes or rhodium carbonyl complexes which are modified with tertiary organic phosphines, at temperatures of from 80° to 200° C under superatmospheric pressure, and the resulting 3-formylpropionaldehyde-acetals and any 4-hydroxybutyraldehyde-acetals produced at the same time are then hydrogenated in the presence of water and hydrogenation catalysts, at elevated temperatures and under superatmospheric pressure.

The process according to the invention has the advantage of good yields and simplicity. It has the further advantage that acrolein, which arises as a by-product of the oxidation of propylene to acrylic acid, is readily obtainable. The cyclic acetals of acrolein are also easily obtainable, as they can be manufactured simply by reaction of acrolein with diols.

The process according to the invention is noteworthy in that it was unforeseeable that the hydroformylation of acrolein-acetals in the presence of phosphine-modified catalysts would succeed. In fact, it is known from Bayer "Lehrbuch der organischen Chemie," 1963 edition, p. 124, that olefinically unsaturated compounds containing polarized double bonds, such as acrylonitrile, acrylic esters and acrolein, polymerize in the presence of phosphines. Thus, even traces of phosphine suffice to initiate the polymerization of free acrolein. In addition the effect of phosphine-modified oxo catalysts was unforeseeable since, according to Kogyo Kagaku Zasshi, 74, No. 8, p. 1,640 to 1,643, dimerization occurs, with degradation of the catalyst, in the case of the hydroformylation of acrylic esters, i.e. of compounds which are chemically very closely related to the acroleinacetals. Hence, it would have been expected that there would be considerable interference with the hydroformylation of acrolein-acetals in the presence of phosphines.

The preferred starting materials are cyclic acrolein-acetals of alkanediols of up to 4 carbon atoms, for example of ethylene glycol, 1,2-propylene glycol, 1,3-propylene glycol, 1,4-butylene glycol or 2-methyl-1,3-propanediol. Acrolein-acetals of 1,3-propanediol, 1,3-butanediol and especially of 2-methyl-1,3-propanediol (since the latter occurs as a by-product of the synthesis) are particularly suitable.

The cyclic acrolein-acetals are obtained by, e.g., treatment of acrolein with a 2M to 3M excess of the diol at temperatures of from 30° to 50° C in the presence of a strongly acid ion exchanger, followed by distillation.

The carbon monoxide and hydrogen are generally employed in a volume ratio of from 1:0.25 to 1:4, especially from 1:0.5 to 1:2. As a rule, at least the stoichiometric amount of gas mixture is employed, but an excess of up to 200 mole percent, based on the acrolein-acetal, is of advantage.

The hydroformylation is carried out at temperatures of from 80° to 200° C, and temperatures of from 100° to 160° C have proved particularly suitable. Advantageous pressures to use are from 5 to 100, and especially from 10 to 80, atmospheres gauge.

The hydroformylation is carried out in the presence of cobalt carbonyl complexes or rhodium carbonyl complexes which have been modified with tertiary organic phosphines. It is possible to use catalyst complexes which have been prepared beforehand, e.g. $Co_2(CO)_6L_2$, $HCo(CO)_3L$, $HRh(CO)L_3$, $ClRh(CO)L_2$ and $L_3RhCl$ (L = tert. phosphine).

However, it is also possible to form the catalyst complexes under the reaction conditions in situ from the corresponding metal carbonyls and the phosphine, or a reactive metal compound, e.g. dicobalt octocarbonyl, cobalt salts of fatty acids, rhodium carbonyl, rhodium carbonyl chloride, rhodium carbonyl acrylate or cyclo-1,5-octadienyl-rhodium chloride, carbon monoxide, hydrogen and the phosphine. In general, the carbonyl complexes are used in amounts of from 100 ppm to 2 percent by weight, in particular from 0.1 to 1.0 percent by weight, calculated as metal and based on the starting materials.

The preferred ligands L are tri-$C_1$-$C_{30}$-alkylphosphines such as trioctylphosphine, tridodecylphosphine, diethyldodecylphosphine or dimethyleicosylphosphine or arylphosphines or aralkylphosphines, especially phenylphosphines or alkylphenylphosphines such as triphenylphosphine, tritolylphosphine, dimethylphenylphosphine or ethylditolylphosphine. The alkyl or aryl radicals can contain functional groups such as methoxy, carbonyl or carbalkoxy groups, as in the case of p-methoxyphenyldimethylphosphine or 10-carboxydecyldimethylphosphine. The use of tri-$C_1$-$C_{20}$-alkylphosphines and triphenylphosphines is particularly preferred. Advantageously, from 1 to 20 moles of alkylphosphines are used per gram atom of cobalt. In the case of rhodium, a combination with arylphosphines, in which from 5 to 50 moles of phosphine are used per gram atom of rhodium, has proved particularly effective.

The reaction can be carried out in the absence of solvents. However, it is also possible to carry out the hydroformylation in the presence of solvents such as hydrocarbons, e.g. benzene, cyclohexane or hexane, ethers, e.g. tetrahydrofuran or dibutyl ether, or alkanols, e.g. butanol.

The hydroformylation can be carried out batchwise or by a simple continuous method in suitable equipment. The resulting reaction products consist essentially of 3-formylpropionaldehyde-acetals and 4-hydroxybutyraldehyde-acetals in addition to minor amounts of the corresponding isomeric compounds, namely the 2-formylpropionaldehydeacetals and 2metyl-3-hydroxypropionaldehyde-acetals which are formed during the hydroformylation.

After completion of the reaction, the solvents and hydroformylation products in the reaction mixture are separated, if desired, from the catalyst residue by conventional methods, e.g. distillation under reduced pressure, and the catalyst residue can be re-used directly in the hydroformylation reaction.

The hydroformulation mixture thus obtained, which essentially consists of 3-formylpropionaldehyde-acetal and 4-hydroxybutyraldehyde-acetal with minor amounts of isomeric compounds and, where relevant, solvents, is hydrogenated in the presence of water and hydrogenation catalysts. The amount of water used is advantageously at least the stoichiometric amount but in particular an up to 30-fold molar excess.

Preferred hydrogenation catalysts are metals of group 8 of the Periodic Table, especially nickel, cobalt and noble metals of group 8, such as platinum or palladium. In industrial practice, copper, nickel and cobalt catalysts have proved particularly suitable. The catalysts can also contain activators such as copper, zinc and chromium. Raney nickel, Raney cobalt and the so-called Adkins catalyst (copper/chromium oxide catalysts) are particularly suitable catalysts.

The catalysts can be used unsupported or on carriers such as silica gel, silica or aluminum oxide. In general, the supported catalysts contain from 5 to 40 percent by weight of the catalytic metals. proved The hydrogenation is advantageously carried out at temperatures of from 70° to 150° C, especially from 80° to 130° C; pressures of from 100 to 300 atmospheres have proved particularly suitable. 1,4-Butanediol is isolated from the hydrogenated material by conventional methods, e.g. by distillation. The alkanediol eliminated from the acetal during the hydrogenation and obtained as a by-product can be re-used to manufacture the acrolein-acetals used as starting materials.

1,4-Butanediol manufactured by the process of the invention can be used for the manufacture of tetrahydrofuran, an important solvent, and for the manufacture of polyesters and also, in particular, polyurethanes.

EXAMPLE 1

Hydroformylation of acrolein-(1,3-butanediol)-diacetal 2.8 g of dicobalt octacarbonyl and 12.1 g of trioctylphosphine, dissolved in 120 g of benzene, are introduced into a pressure reactor of 2 l capacity, which is equipped with a stirrer. The reactor is then flushed twice with a gas mixture of 1 part by volume of carbon monoxide and 2 parts by volume of hydrogen. After heating the mixture to 150° C, the pressure is set to 70 atmospheres by means of the above gas mixture. A mixture of 120 g of acrolein-(1,3-butanediol)-diacetal and 80 g of benzene is then introduced in four portions into the reaction vessel, in the course of 2 hours. The pressure is maintained at from 70 to 80 atmospheres by replenishing with the above gas mixture. After 2 hours, the total amount of gas taken up is equivalent to a 36 atmospheres pressure change. Analysis of the reaction product by gas chromatography indicates the following composition (ignoring solvent and catalyst): 13.9% of acrolein-acetal and propionaldehyde-acetal, 67.2% of 2-formyl- and 3-formylpropionaldehyde-acetal and 18.9% of 4-hydroxybutyraldehyde-acetal and 2-hydroxyisobutyraldehyde-acetal. 81% of the hydroformylation products are accounted for by linear isomers.

EXAMPLE 2

Hydroformylation of acrolein-(2-methyl-1,3-propanediol)-diacetal

The procedure followed is a described in Example 1 but the reactor is charged with 96 g of acrolein-(2-methyl-1,3-propanediol)-diacetal, 4.3 g of dicobalt octacarbonyl and 26 g of dimethylalkylphosphine (with alkyl of 20 to 26 carbon atoms). After 2 hours reaction time the total amount of gas taken up is equivalent to a 38 atmospheres pressure change. Analysis of the reaction product by gas chromatography indicates that 82% of linear isomers are present. The product is then distilled, benzene being removed first. 13 g of the propionaldehyde-acetal and 108 g of acetals of the actual oxo products are obtained (representing 89% of the amount theoretically expected), together with 36 g of residue.

EXAMPLE 3

Manufacture of 1,4-butanediol

The 108 g of the oxo product from Example 2 are hydrogenated with 400 ml of methanol, 100 ml of water and 40 g of Raney nickel (which has been carefully washed until neutral) for 5 hours at 280 atmospheres and a maximum temperature of 140° C. The catalyst is then filtered off, the solvent is stripped off and the butanediols are distilled at from 93° to 96°C/2mm. 105 g of diols are obtained, containing 60% of 2-methyl-1,3-propanediol and 40% of 1,4-butanediol, according to gas-chromatographic analysis of the diacetates. This means, taking into account the branched isomer employed as the acetalization component, that the newly formed diol comprises 80% of linear isomer, i.e. 1,4-butanediol and 20% of branched isomer, i.e. 2-methyl-1,3-propanediol. On distillation under reduced pressure (10 mm Hg) the branched isomer passes over at 97° C and the 1,4-butanediol at 111° C.

EXAMPLE 4

Hydroformylation of acrolein-(1,3-propanediol)-diacetal 450 ml of benzene, 0.51 g of HRhCO(P($C_6H_5$)$_3$)$_3$ (= 0.55 milliequivalent of Rh) and 5.8 g of triphenylphosphine (= 22 millimoles) are introduced into a pressure reactor of 2 l capacity, which is equipped with a stirrer. The reactor is flushed three times with a gas mixture of 1 part by volume of carbon monoxide and 1 part by volume of hydrogen. After heating to 140° C, the pressure is set to 40 atmospheres by means of the said gas mixture. 100g of acrolein-(1,3-propanediol)-diacetal are then introduced into the reactor. During the reaction, the pressure is kept at from 20 to 40 atmospheres by replenishing with the above gas mixture. The absorption of gas ceases after 45 minutes. At this stage, the analysis of the reaction product by gas chromatography shows traces of the starting material, and a mixture of 2-formyl- and 3-formyl-propionaldehyde-acetal in the ratio of 32:68. Accordingly, no hydrogenated products are obtained, in contrast to the case of the cobalt catalyst.

The product is again distilled, and 112 g (= 89% of theory) of formyl compounds and 10 g of residue are obtained.

EXAMPLE 5

Manufacture of 1,4-butanediol

The 112 g of the formyl compounds obtained according to Example 4 are hydrogenated with 250 g of water and 25 g of Raney cobalt (which have been carefully washed until neutral) in an autoclave, initially for 5 hours at 80° C and 160 atmospheres and then for 5 hours at 130° C and 280 atmospheres. The catalyst is filtered off and the water is distilled off, after which 120 g of diol mixture are obtained at from 90° to 95° C/2 mm Hg. A sample is esterified with acetic anhydride and examined by gas chromatography; this shows the presence of 45% of 1,3-propanediol, 15.0% of 2-methyl-1,3-propanediol and 40.0% of 1,4-butanediol. Accordingly, 72.5% of the diols newly formed are unbranched. The diol mixture can be separated by distillation, as described in Example 3.

I claim:

1. A process for the manufacture of 1,4-butanediol, wherein cyclic acetals of acrolein are reacted with carbon monoxide and hydrogen in the presence of cobalt carbonyl complexes or rhodium carbonyl complexes which are modified with tertiary organic phosphines, at temperatures of from 80° to 200° C under superatmospheric pressure, and the resulting 3-formylpropionaldehyde-acetals and the 4-hydroxybutyraldehyde-acetals produced are hydrogenated in the presence of water at 70°-150° C and under superatmospheric pressure in the presence of a hydrogenation catalyst containing a metal of group 8 of the Periodic Table or copper as a catalytically active metal.

2. A process as claimed in claim 1, wherein the acetal of acrolein with 2-methyl-1,3-propanediol is used as the starting material.

3. A process as claimed in claim 1, wherein tri-$C_1$- to $C_{20}$-alkylphosphines or triphenylphosphine are used as modifiers in the hydroformylation reaction.

4. A process as claimed in claim 1, wherein, in the case of rhodium catalysts, from 5 to 50 moles of tertiary organic phosphines are employed per gram atom of rhodium.

5. A process as claimed in claim 1, wherein, in the case of cobalt catalysts, from 1 to 20 moles of tertiary organic phosphines are employed per gram atom of cobalt.

6. A process as claimed in claim 1, wherein from 1 to 30 moles of water are employed in the hydrogenation reaction, per mole of the hydroformylation products first obtained.

7. A process as claimed in claim 1 wherein said tertiary organic phosphine is a tri-$C_1$ to $C_{30}$-alkyl phosphine, a triarylphosphine, a tertiary alkylphenyl phosphine, or one of said phosphines having one or more methoxy, carbonyl or carbalkoxy groups.

8. A process as claimed in claim 1 wherein said tertiary organic phosphine is a tri-$C_1$ to $C_{30}$-trialkylphosphine.

9. A process as claimed in claim 1 wherein said tertiary organic phosphine is triphenylphosphine or tritolylphosphine.

10. A process as claimed in claim 1 wherein said hydrogenation catalyst is a nickel, cobalt or copper hydrogenation catalyst.

11. A process as claimed in claim 1 wherein said catalyst contains, as an activator, copper, zinc or chromium.

12. A process as claimed in claim 1 wherein said hydrogenation catalyst is Raney nickel or Raney cobalt.

13. A process as claimed in claim 1 wherein said hydrogenation catalyst is an adkins copper/chromium oxide hydrogenation catalyst.

14. A process for preparing 1,4-butanediol which comprises hydroformylating a cyclic acetal of acrolein and an alkanediol of up to 4 carbon atoms in the presence of a cobalt carbonyl complex or a rhodium carbonyl complex, said complexes being modified by a tertiary organic phosphine, at temperatures of from 80° to 200° C under superatmospheric pressure to produce the corresponding cyclic acetals of formylpropionaldehydes, and hydrogenating the corresponding cyclic acetals of formylpropionaldehydes at elevated temperatures and under superatmospheric pressure in the presence of a hydrogenation catalyst and in the presence of water.

15. A process as claimed in claim 14 wherein said cyclic acetal is the cyclic acetal of acrolein and 1,3-propanediol, 1,3-butanediol, or 2-methyl-1,3-propanediol.

16. A process as claimed in claim 14 wherein the hydrogenation is carried out at 70-150° C and at superatmospheric pressure in the presence of a catalytic amount of a hydrogenation catalyst containing a metal of group 8 of the Periodic Table or copper as a catalytically active metal.

17. A process for preparing 1,4-butanediol which comprises hydroformylating a cyclic acetal of acrolein and 2-methyl-1,3-propanediol in the presence of a cobalt carbonyl complex or a rhodium carbonyl complex, said complexes being modified by a tertiary organic phosphine, at temperatures of from 80° to 200° C and superatmospheric pressure to produce formylpropionaldehyde acetals of 2-methyl-1,3-propanediol, and hydrogenating the resulting acetals at elevated temperatures and pressure in the presence of water and in the presence of a hydrogenation catalyst to produce a mixture of 1,4-butanediol and 2-methyl-1,3-propanediol.

18. A process as claimed in claim 17 wherein said formylpropionaldehyde acetals of 2-methyl-1,3-propanediol are hydrogenated in the presence of from at least the stoichiometric amount up to a 30-fold molar excess of water at a temperature of 70° – 150° C. and a pressure of 100 – 300 atmospheres.

* * * * *